US00PP14372P29

(12) United States Plant Patent
Trees

(10) Patent No.: US PP14,372 P2
(45) Date of Patent: Dec. 16, 2003

(54) JAMESBRITTENIA PLANT NAMED 'BALBREUPIT'

(50) Latin Name: *Jamesbrittenia grandiflora*
Varietal Denomination: Balbreupit

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/329,663

(22) Filed: Dec. 26, 2002

(51) Int. Cl.[7] ..... A01H 5/00
(52) U.S. Cl. ..... Plt./263
(58) Field of Search ..... Plt./263

(56) References Cited

U.S. PATENT DOCUMENTS

| | | | | | |
|---|---|---|---|---|---|
| PP10,966 | P | * | 6/1999 | Rother | Plt./263 |
| PP11,835 | P2 | * | 4/2001 | Rother | Plt./263 |
| PP12,682 | P2 | * | 6/2002 | Polman | Plt./263 |
| PP12,689 | P2 | * | 6/2002 | Churchus | Plt./263 |

* cited by examiner

*Primary Examiner*—Bruce R. Campell
*Assistant Examiner*—W C Haas
(74) *Attorney, Agent, or Firm*—Wood, Phillips, Katz, Clark & Mortimer

(57) ABSTRACT

A new and distinct Jamesbrittenia plant named "Balbreupit", characterized by its white flowers, upright growth habit, and dark green leaves.

1 Drawing Sheet

Latin name of the genus and species of plant claimed: *Jamesbrittenia grandiflora.*
Variety denomination: 'Balbreupit'.

BACKGROUND OF THE INVENTION

The present invention comprises a new and distinct Jamesbrittenia plant, botanically known as *Jamesbrittenia grandiflora*, and hereinafter referred to by the name 'Balbreupit'.

'Balbreupit' originated from the open pollination of a *Jamesbrittenia grandiflora* selection designated BRD-018 (not patented) during October 2000. The new cultivar was discovered by the inventor during February 2001, in a controlled environment at Arroyo Grande, Calif.

Asexual reproduction of the new cultivar, in Arroyo Grande, Calif. and West Chicago, Ill., by terminal tip cuttings has demonstrated that the characteristics of the new cultivar as herein described are firmly fixed and retained through successive generations of such asexual propagation.

SUMMARY OF THE INVENTION

It was found that the cultivar of the present invention:

(a) exhibits white flowers, (b) forms medium green foliage, (c) exhibits a good basal branching character, and (d) exhibits an upright growth habit.

The new cultivar of the present invention can be compared to 'Bridal showers' (not patented). In side-by-side comparisons, plants of the new cultivar exhibit a taller growth habit and have longer branches but shorter internodes than 'Bridal showers'.

BRIEF DESCRIPTION OF PHOTOGRAPH

The accompanying photographs show as nearly true as it is reasonably possible to make the same in color illustrations of this type, typical flower and foliage characteristics of the new cultivar. Colors are as accurately represented as can be made by conventional photography. The plants were grown in 10 cm pots for 10 weeks in a greenhouse at West Chicago, Ill., U.S.A.

DETAILED BOTANICAL DESCRIPTION

Figure 1:
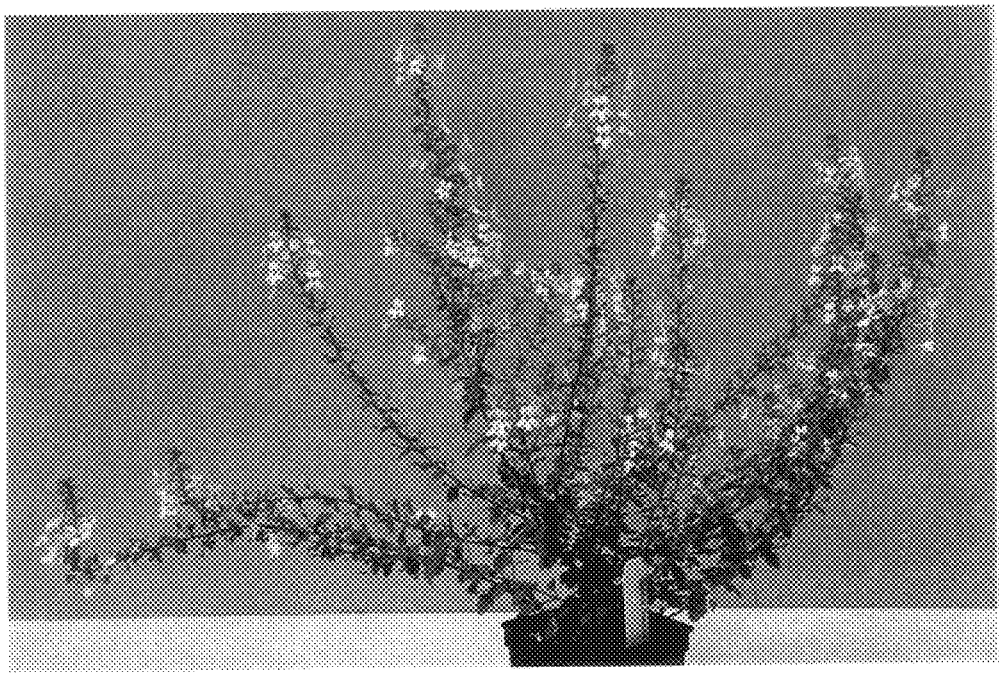
FIG. 1 illustrates the overall plant form of 'Balbreupit'.
Figure 2:
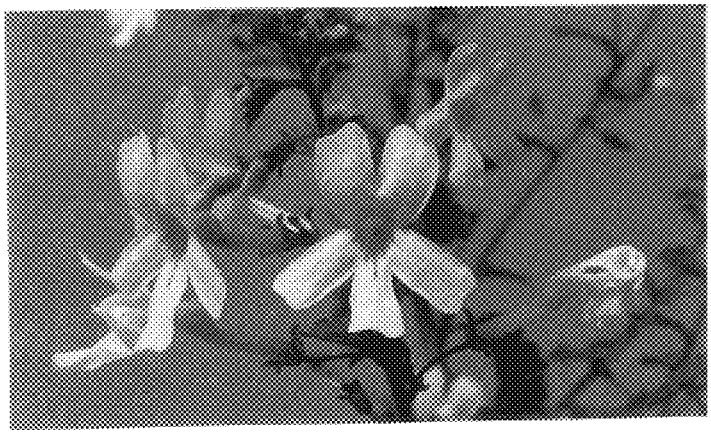
FIG. 2 illustrates a close-up view of foliage and individual flowers of 'Balbreupit'.

'Balbreupit' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Oct. 15, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice while utilizing a soilless growth medium and maintaining temperatures of approximately 65–75° F. during the day and approximately 55–60° F. during the night and light levels of approximately 4,000 to 8,000 footcandles Plants used for the following descriptions and measurements were grown for 10 weeks from rooted cuttings.

Classification:
*Botanical.*—*Jamesbrittenia grandiflora* cultivar 'Balbreupit'.
*Common name.*—Bacopa.

Parentage: Open pollination of *Jamesbrittenia grandiflora* selection designated BRD-018.

Propagation:

*Type cutting.*—Terminal tip.

*Time to initiate roots.*—Approximately 7 to 10 days.

*Time to develop roots.*—Approximately 21 to 30 days.

*Root description.*—Fibrous, branching.

Plant description:

*Habit of growth.*—Moderately vigorous with good basal branching. Pinching improves basal branching. A mature plant, 10 weeks after the planting of a rooted cutting, commonly measures approximately 48.2 cm in height and approximately 33.2 cm in diameter with an average of 8.7 branches.

*Form.*—Spreading and trailing.

*Branch.*—Length: Approximately 45.6 cm. Diameter: Approximately 2 mm. Texture: Punctate. Color: 144A Internode length at middle of branch is approximately 1.5 cm.

*Foliage.*—Fragrance: Pungent. Form: Simple. Arrangement: Alternate, at an acute angle to the stem. Shape: Ovate with lobed margin, obtuse apex and attenuate base. Upper and lower surfaces are punctate. Leaf length is approximately 1.3 cm and width is approximately 1 cm. Upper surface of both young and mature foliage is 137B; lower surface of both young and mature foliage is 138A. Both upper and lower surfaces have pinnate venation closest to 143B. Petiole length is approximately 3 mm, diameter is approximately 1 mm, surface is densely pubescent and color is closest to 143B.

Flowering description:

*Flowering habit.*—Freely flowering.

*Natural flowering season.*—Year round in greenhouse environment; April through October in outdoor garden.

*Flower type.*—Solitary, axillary and salverform. Flowers are persistent.

*Peduncle.*—Moderately strong. Texture: Punctate. Aspect: At an acute angle to the stem. Length: Approximately 9 mm. Diameter: Less than 1 mm. Color: Slightly more yellow than 138A.

*Bud.*—Club shaped, approximately 1.3 cm in length, 3 mm in diameter. Color: 150C.

*Flower description.*—Non-fragrant. Corolla is round, approximately 1.6 cm in diameter composed of five (5) rectangular shaped petals. Petals are iridescent, approximately 5 mm long and 3 mm wide, have an entire margin and flat to somewhat emarginated tip. Color of upper surface of petals when flower is opening and when fully opened is closest to 155D with base around tube opening and into tube of 151C and venation of 12A at base. Color of lower surface of petals both when opening and when fully opened is closest to 155D. Corolla tube is approximately 1.2 cm in length, 2 mm in diameter, and pubescent on both inner and outer surface. Color of both inner and outer surface of tube is 154D.

*Calyx.*—Five parted tube fused at base. Approximately 3 mm in length. Sepals are spatulate, less than 1 mm in width, have an acute apex, entire margin. The both surfaces are punctate and 138A.

*Reproductive organs.*—Androecium: There are 4 stamens fused to the inside of the corolla tube, 2 above and 2 below the stigma. Anther length: Approximately 1 mm. Anther color: 7B. Pollen amount: Abundant. Pollen color: 13B. Gynoecium: One pistil, approximately 9 mm in length. Stigma length: Approximately 1 mm. Stigma color: 144C. Style length: Approximately 6 mm. Style color: N144C. Ovary diameter: Approximately 2 mm. Ovary color: 144C.

Seed production: Seed production has not been observed.

Disease resistance: Resistance to pathogens has not been observed.

I claim:

1. A new and distinct *Jamesbrittenia grandiflora* plant named 'Balbreupit' substantially as herein shown and described, which:

(a) exhibits white flowers, (b) forms medium green foliage, (c) exhibits a good basal branching character, and (d) exhibits an upright growth habit.

* * * * *